US012760256B2

(12) United States Patent
Yang et al.

(10) Patent No.: US 12,760,256 B2
(45) Date of Patent: Oct. 13, 2026

(54) CONFINED MIGRATION MICROFLUIDIC DEVICE FOR CELL CULTURE AND DRUG SCREENING

(71) Applicant: City University of Hong Kong, Hong Kong (CN)

(72) Inventors: Mengsu Yang, Hong Kong (CN); Zihan Yang, Hong Kong (CN); Zhihang Zhou, Hong Kong (CN); Tongxu Si, Hong Kong (CN); Zhengdong Zhou, Hong Kong (CN)

(73) Assignee: City Unversity of Hong Kong, Hong Kong (CN)

( * ) Notice: Subject to any disclaimer, the term of this patent is extended or adjusted under 35 U.S.C. 154(b) by 1051 days.

(21) Appl. No.: 17/822,209

(22) Filed: Aug. 25, 2022

(65) Prior Publication Data

US 2023/0374430 A1 Nov. 23, 2023

(30) Foreign Application Priority Data

May 19, 2022 (CN) ......................... 202210557883.0

(51) Int. Cl.

*C12M 3/00* (2006.01)
*C12M 1/12* (2006.01)
*C12M 3/06* (2006.01)

(52) U.S. Cl.

CPC ............ *C12M 23/16* (2013.01); *C12M 23/42* (2013.01); *C12M 23/48* (2013.01); *C12M 25/00* (2013.01)

(58) Field of Classification Search

None

See application file for complete search history.

(56) References Cited

U.S. PATENT DOCUMENTS

2010/0035292 A1* 2/2010 Levhenko ............... B01F 35/81 435/283.1
2011/0306041 A1* 12/2011 Viovy .................. C12N 5/0619 435/7.1

(Continued)

FOREIGN PATENT DOCUMENTS

CN 106497771 * 3/2017
CN 110713923 * 1/2020

(Continued)

OTHER PUBLICATIONS

Paul CD, Mistriotis P, Konstantopoulos K. Cancer cell motility: lessons from migration in confined spaces. Nat Rev Cancer. 2017;17:131-40.

(Continued)

*Primary Examiner* — Michael A Marcheschi
*Assistant Examiner* — Nathan G Esperon
(74) *Attorney, Agent, or Firm* — S&F/WEHRW

(57) ABSTRACT

Provided is a confined migration microfluidic device for cell culture and drug screening, including a chip including a plurality of parallel channels, where each pair of it is connected through a plurality of the confined migration channels; a depth of the confined migration channel is lower than the first channel and second channel; a first/second inlet and a first/second outlet are provided at two ends of the first/second channel, respectively; and a pyramid-like structure for diverging flow to the first channels to ensure evenly distribution. During the usage, cells to be cultured are added into one of the first channel and the second channel, and drugs or cells which can influence confined migration of the target cells are added into the other channel; the inhibitory effect of the drugs or cells on the confined migration will be evaluated, thereby screening/studying effective drugs and cells in relation to the confined migration.

17 Claims, 5 Drawing Sheets

(56) References Cited

U.S. PATENT DOCUMENTS

| | | | | |
|---|---|---|---|---|
| 2016/0186112 A1* | 6/2016 | Magdesian | B01L 3/502715 | |
| | | | 435/325 | |
| 2019/0344270 A1* | 11/2019 | Yoon | B01L 3/502738 | |

FOREIGN PATENT DOCUMENTS

| | | | |
|---|---|---|---|
| CN | 210613744 | * | 5/2020 |
| CN | 111218401 | * | 6/2020 |
| CN | 112980677 | * | 6/2021 |

OTHER PUBLICATIONS

Tong Z, Balzer EM, Dallas MR, Hung W-C, Stebe KJ, Konstantopoulos K. Chemotaxis of cell populations through confined spaces at single-cell resolution. PLoS One. 2012;7:e29211.

Zou H, Yang Z, Chan Y-S, Yeung SA, Alam MK, Si T, et al. Single cell analysis of mechanical properties and EMT-related gene expression profiles in cancer fingers. iScience. 2022;25:103917.

Chen YC, Allen SG, Ingram PN, Buckanovich R, Merajver SD, Yoon E. Single-cell migration chip for chemotaxis-based microfluidic selection of heterogeneous cell populations. Sci Rep. 2015;5.

Schuster B, Junkin M, Kashaf SS, Romero-Calvo I, Kirby K, Matthews J, et al. Automated microfluidic platform for dynamic and combinatorial drug screening of tumor organoids. Nat Commun. 2020;11:1-12.

Fan X, Deng Z, Yan Y, Orel VE, Shypko A, Orel VB, et al. Application of microfluidic chips in anticancer drug screening. Bosn J Basic Med Sci. 2022;22:302.

Balzer EM, Tong Z, Paul CD, Hung W-C, Stroka KM, Boggs AE, et al. Physical confinement alters tumor cell adhesion and migration phenotypes. The FASEB Journal. 2012;26:4045.

Dittrich PS, Manz A. Lab-on-a-chip: microfluidics in drug discovery. Nat Rev Drug Discov. 2006;5:210-8.

Wu M-H, Huang S-B, Lee G-B. Microfluidic cell culture systems for drug research. Lab Chip. 2010;10:939-56.

Kohl Y, Biehl M, Spring S, Hesler M, Ogourtsov V, Todorovic M, et al. Microfluidic in vitro platform for (nano) safety and (nano) drug efficiency screening. Small. 2021;17:2006012.

Jiang Y, Zhang H, Wang J, Liu Y, Luo T, Hua H. Targeting extracellular matrix stiffness and mechanotransducers to improve cancer therapy. J Hematol Oncol. 2022;15:1-15.

Sala F, Ficorella C, Osellame R, Kás JA, Martínez Vázquez R. Microfluidic Lab-on-a-Chip for Studies of Cell Migration under Spatial Confinement. Biosensors (Basel). 2022;12:604.

Paul CD, Hung W-C, Wirtz D, Konstantopoulos K. Engineered models of confined cell migration. Annu Rev Biomed Eng. 2016;18:159.

Zhang Y, Zhang W, Qin L. Mesenchymal-mode migration assay and antimetastatic drug screening with high-throughput microfluidic channel networks. Angewandte Chemie. 2014;126:2376-80.

Zhou M, Ma Y, Chianga C, Rock EC, Luker KE, Luker GD, et al. High-Throughput Cellular Heterogeneity Analysis in Cell Migration at the Single-Cell Level. Small. 2022;2206754.

* cited by examiner

CONFINED MIGRATION MICROFLUIDIC DEVICE FOR CELL CULTURE AND DRUG SCREENING

CROSS-REFERENCE TO RELATED APPLICATION

This application claims priority from a Chinese patent application number 202210557883.0 filed May 19, 2022, and the disclosure of which is incorporated herein by reference in its entirety.

TECHNICAL FIELD

The present invention relates to medical devices, in particular, to a microfluidic chip for cell culture and drug screening, and more particularly, to a confined migration microfluidic device for cell culture and drug screening.

BACKGROUND

Cancer is one of the leading causes of death today and it causes about 9 million deaths each year worldwide. The mortality rate of cancer is low if it is found at an early stage, but the mortality rate will be greatly increased once the cancer metastasizes. Metastasis of cancer cells is the leading cause of cancer-induced deaths.

Currently, metastasis involves several sequential steps, specifically invasion, penetration into the vessels, circulation, and penetration out of the vessels. However, the 4 steps described above are extremely complex, and metastasis is the least well-known process in tumor progression. Cell migration is a key process of cancer metastasis, and because the hardness and mechanical properties of tumor tissues are significantly different from those of normal tissues, migration of cancer cells is faced with more severe migration conditions. In particular, during metastasis, cancer cells are stimulated by a variety of mechanical forces, including stromal and hydrodynamic forces. A large amount of extracellular matrix builds up in the solid tumor microenvironment, forming many restrictive micropores or microchannels for cell migration. For example, the arrangement and binding of collagen fibers around tumors provide clues for directed migration; cells may also migrate through unbound extracellular matrix (ECM), such as fibrillar collagen, which presents porous migration spaces; micro-tracking also occurs within and around blood vessels; cells may also migrate between epithelial and endothelial surfaces. Therefore, the confined migration of cancer cells is one of the key steps of tumor metastasis. However, there is no effective condition for simulating the confined migration of cancer cells at present, let alone knowing which drugs or cells can effectively block the confined migration of cancer cells and thereby prevent the metastasis of cancer cells, and therefore it is particularly difficult to find effective drugs or associated cells or tissues that restrict metastasis of cancer cells.

In view of the prior arts, there is an urgent need to establish an device capable of simulating the confined migration of cancer cells and a screening device capable of screening drugs or cells for restricting the migration of cancer cells on a platform.

SUMMARY OF THE INVENTION

Accordingly, to solve the problems described hereinabove, the present invention provides a confined migration microfluidic device for cell culture and drug screening.

In one aspect, there is provided a confined migration microfluidic device for cell culture and drug screening including:

a plurality of first channels;

a plurality of second channels disposed in parallel with the first channels thereby providing a plurality of pairs of the first channels and the second channels;

a first inlet and a first outlet respectively disposed at two opposite ends of each of the first channels;

a second inlet and a second outlet respectively disposed at two opposite ends of each of the second channels; and a plurality of confined migration channels each having two extension channels composed of a first extension channel and a second extension channel respectively disposed at two opposite ends of each of the confined migration channels, where:

each of the plurality of pairs of the first and second channels are connected with each other through the plurality of confined migration channels such that the first of extension channels connects the first channel and the confined migration channel while the second of extension channels connects the second channel and the confined migration channel;

each of the confined migration channels has a depth smaller than that of the first channel and that of the second channel;

each of the first and second extension channels has a depth greater than that of the confined migration channel;

the plurality of the first channels and second channels are provided on a microfluidic chip such that confined migration cell culture and assays on potential effects of different drug candidates and co-culture of different cells on the confined migration of one or more target cells can be performed on the same microfluidic chip, simplifying operational procedures and enabling high throughput assays.

In certain embodiments, the disposition of the second inlet and second outlet at the two opposite ends of each of the second channels allows different potential drug candidates or cells are introduced through different channels for different assays and screening.

In certain embodiments, each microfluidic chip further includes converging channels each disposed at two opposite ends of each of the first channels corresponding to an inlet converging channel and an outlet converging channel, respectively, and channelizing all the first channels such that the introduced cells or drug candidates to different first channels are identical to each other.

In certain embodiments, the microfluidic chip further includes an outlet connection channel for connecting the first outlet and the outlet converging channel.

In certain embodiments, the microfluidic chip further includes a pyramid-like flow diverging structure, where the number of flow channels at the most bottom (last) gradient level of the pyramid-like flow diverging structure is equal to the number of the first channels.

In certain embodiments, the pyramid-like flow diverging structure is a gradient flow structure, where one flow channel is added to each subsequent gradient level with respect to a preceding gradient level, so as to diverge the flow more evenly.

In certain embodiments, the pyramid-like flow diverging structure includes multiple gradient flow channels, where each gradient level includes a lateral channel and a longitudinal channel; the longitudinal channel of a preceding gradient level channelizes the lateral channel of a subsequent gradient level; and each of the lateral channels of the last gradient level channelizes each of the first channels.

In certain embodiments, the top gradient level of the pyramid-like flow diverging structure includes only a first diverging channel channelizing the first inlet and the lateral channel at a second gradient level.

In certain embodiments, the microfluidic chip includes an upper chip and a lower chip, where the upper chip is provided therethrough the first inlet, the first outlet, the second inlet, and the second outlet; the upper and lower chips are associated with each other to form the microfluidic chip, where the first channel, second channel, first extension channel, second extension channel and confined migration channels are formed between the upper and lower chips.

In certain embodiments, the upper chip includes an upper channel section; the lower chip includes a lower channel section; combination of the upper channel section and the lower channel section forms all types of channels of the microfluidic chip.

In certain embodiments, one or more of the chips is/are polygonal or circular.

In certain embodiments, one or more of the chips is/are octagonal.

In certain embodiments, a cell adhesion reinforcement agent is added onto the interior surface of the channels.

Preferably, the cell adhesion reinforcement agent is fibronectin.

In certain embodiments, the microfluidic device further includes an accommodation structure for accommodating multiple chips, where the accommodation structure includes a plurality of slots/holes.

In certain embodiments, the slots or holes capable of accommodating the chips are circular slots or holes for ease of placement and removal.

Provided herein also is a method for preparing the microfluidic chip, where the method includes:

- constructing a chip template corresponding to microstructures of the upper and lower chips via soft lithography, where the chip template material is silicon oxide wafer;
- mixing polydimethylsiloxane (PDMS) with a curing agent in a ratio under vacuum to obtain a prepared PDMS without microbubbles;
- pouring the prepared PDMS into the chip template, followed by degassing PDMS until completely attached on the silicon oxide wafer;
- drying the PDMS in a desiccator or oven until completely cured and molded;
- cutting the cured and molded PDMS into a single structure and using a circular hole punch to punch holes on the single structure at where the first inlet, first outlet, second inlet and second outlet are disposed;
- treating the single structure by an air plasma treatment system, followed by aligning the single structure under microscopy for bonding;
- sterilizing the single structure under UV before adding fibronectin in a cell culture compartment for reinforcing cell adhesion.

In certain embodiments, the cells are normal cells or abnormal (disease) cells, or both.

In certain embodiments, the normal cells include kidney cells, lung cells, gastrointestinal cells, brain cells, liver cells, fibroblasts, endothelial cells, immune cells and macrophages.

In certain embodiments, the disease cells include tumor cells, tumor-associated macrophages or tumor-associated fibroblasts.

In certain embodiments, the tumor cells include gastric cancer cells, pancreatic cancer cells, colorectal cancer cells, liver cancer cells, bone cancer cells, lung cancer cells, kidney cancer cells, prostate cancer cells, breast cancer cells, brain cancer cells, neuroendocrine tumor (cancer) cells and all other tumor cells associated thereto.

The present invention further provides a method of using the microfluidic chip or device described herein for screening substances with potentials of inhibiting confined migration of tumor cells.

The present invention further provides a method of using the microfluidic chip or device described herein for screening drug candidates with potentials of inhibiting confined migration of tumor cells.

The present invention further provides a method of using the microfluidic chip or device described herein for screening cells with potentials of inhibiting confined migration of tumor cells.

The present invention further provides a method of using the microfluidic chip or device described herein in preparing a medicament for inhibiting confined migration of tumor cells.

Some of the beneficial effects of the present invention are summarized, as follows: the chip described herein can be used for well observing the confined migration of a type of cancer cells. It can also be used to observe the interference effect of different drugs on the cell migration after the different drugs are used on the other side of the confined channel, and thus effective drug candidates of inhibiting the cell migration can be determined for potential cancer treatment. Effects of different concentrations of the same drug on cell migration can also be evaluated, where a therapeutically effective amount of migration-inhibiting drug can also be determined, or the effect of the same drug at the same concentration on the migration of different cells can be evaluated. It can also be used to evaluate any combined effect of co-culture and drug on cell migration. The provision of pyramid-like flow diverging channel configuration on a single chip ensures consistency in concentration and quantity of the introduced drugs or cells in each channel, reducing errors to the greatest extent, and improving operation and evaluation efficiency due to the presence of sufficient number of drug screening channels. In addition, the plural confined migration channels extending out of each drug screening channel can further be used to evaluate the possibility of multiple confined migrations and migration inhibition by potential drug candidates, which may be realized under the same condition, and thus multiple confined migrations are possible to be evaluated, and errors arising from such evaluation can be significantly reduced due to high specificity. The present microfluidic chip or device is simple to use, and is able to deliver more evaluation data with higher accuracy, that is, high throughput assay under a consistent testing condition can be achieved by the present chip or device.

This summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. Other aspects of the present invention are disclosed as illustrated by the embodiments hereinafter.

BRIEF DESCRIPTION OF DRAWINGS

The appended drawings, where like reference numerals refer to identical or functionally similar elements, contain figures of certain embodiments to further illustrate and clarify the above and other aspects, advantages and features of the present invention. It will be appreciated that these drawings depict embodiments of the invention and are not intended to limit its scope. The invention will be described and explained with additional specificity and detail through the use of the accompanying drawings in which.

Skilled artisans will appreciate that elements in the figures are illustrated for simplicity and clarity and have not necessarily been depicted to scale.

DETAILED DESCRIPTION OF THE INVENTION

It will be apparent to those skilled in the art that modifications, including additions and/or substitutions, may be made without departing from the scope and spirit of the invention. Specific details may be omitted so as not to obscure the invention; however, the disclosure is written to enable one skilled in the art to practice the teachings herein without undue experimentation.

Example 1

Figure 1:
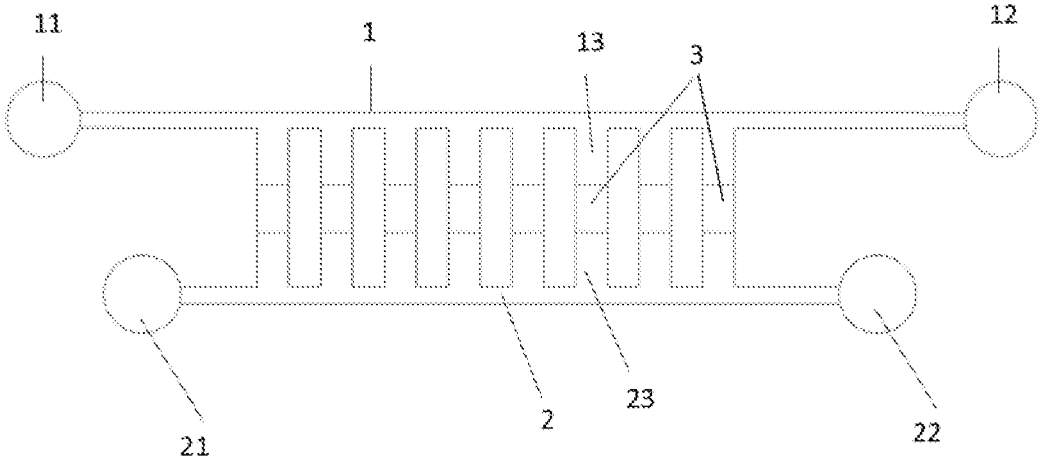
FIG. 1 shows a top view of the structure of an embodiment of the present invention, in which a first channel, a second channel and a plurality of confined migration channels are present.

Turning to FIG. 1, a confined migration microfluidic device for cell culture and drug screening is provided including a microfluidic chip, where the microfluidic device includes a first channel 1 and a second channel 2 disposed in parallel with the first channel 1 to provide a pair of the first channel and second channel; the pair of the first channel 1 and the second channel 2 are connected through confined migration channels 3; a depth of each of the confined migration channels 3 is smaller than that of the first channel 1 and that of the second channel 2; a first inlet 11 and a first outlet 12 are provided at two different (opposite) ends of the first channel 1, respectively, and a second inlet 11 and a second outlet 22 are provided at two different (opposite) ends of the second channel 2, respectively. When the device is used, cells to be cultured are added into one of the first channel 1 and the second channel 2, and drugs or cells which may influence confined migration of the cells are introduced into the other channel; the drugs or other cells are added after the cells are introduced into the channel and begin to migrate through the confined migration channels 3. In certain embodiments, the confined migration channels 3 provided between the first channel 1 and the second channel 2 are identical such that errors arising from observing only one confined migration channel is present.

In certain embodiments, four to ten identical confined migration channels 3 are provided between the first channel 1 and the second channel 2; there may be four, six, eight and ten confined migration channels.

Figure 4:
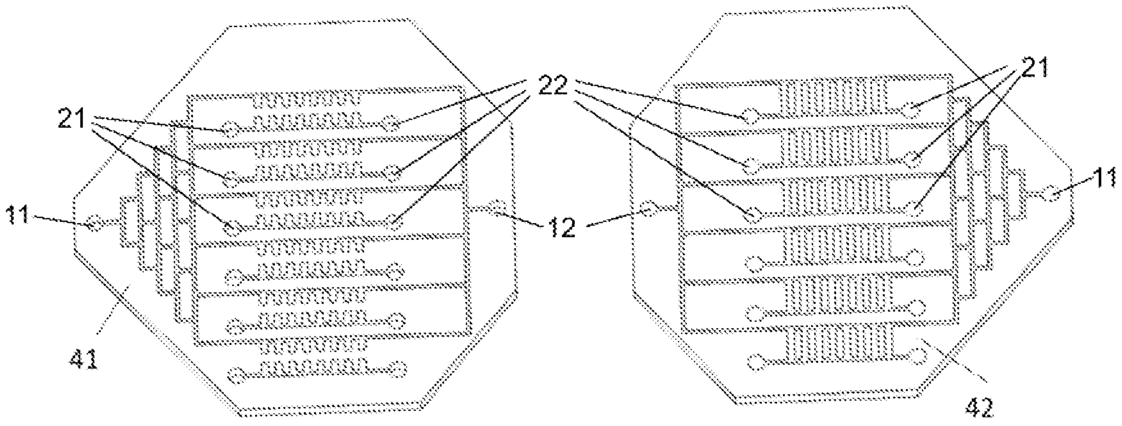
FIG. 4 schematically depicts the structure of the upper chip and the lower chip being separately placed and mirrored by each other according to certain embodiments of the present invention.
Figure 5:
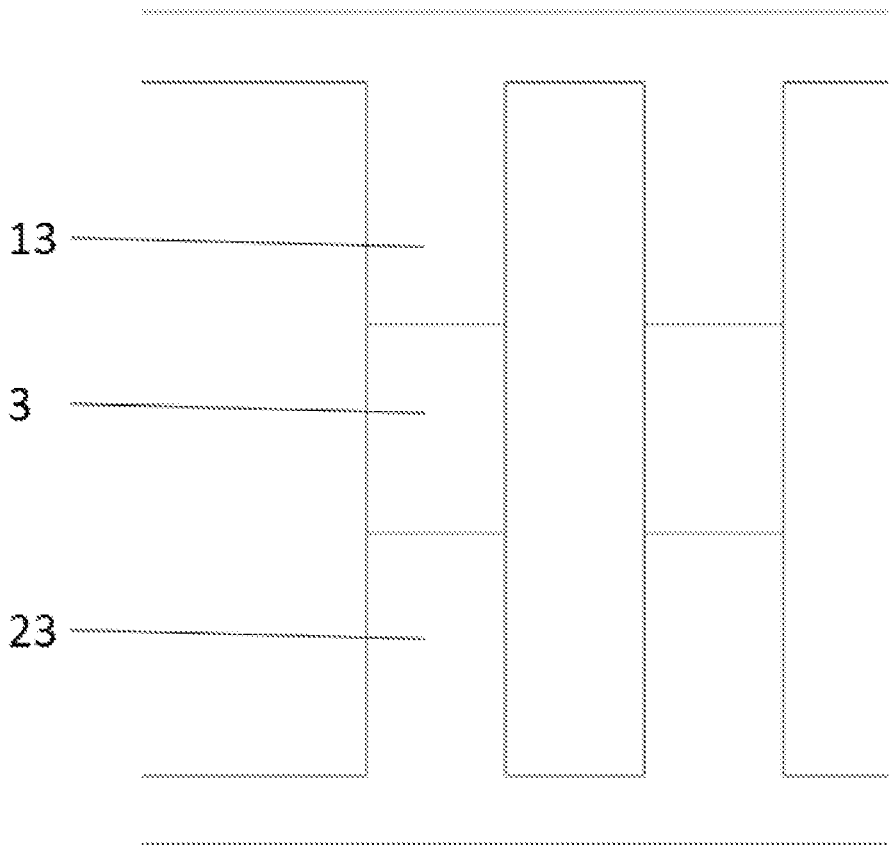
FIG. 5 shows a partially enlarged view of the structure of two confined migration channels according to certain embodiments of the present invention.

In certain embodiments, two extension channels, namely a first extension channel 13 and a second extension channel 23, are provided at two different (opposite) ends of each of the confined migration channels 3, respectively, where the first extension channel 13 connects the first channel 1 and the confined migration channel 3; the second extension channel 23 connects the second channel 2 and the confined migration channel 3; and a depth of the first extension channel 13 and a depth of the second extension channel 23 are each greater than that of each of the confined migration channels 3. This configuration ensures that the cells can be completely subject to confined migration after entering the extension channels, which is more similar to the real migration condition and can avoid the situation that cells will grow along the interior surface of the channels and thereby no migration will occur, in turn, the actual effect and efficiency can not be exerted. Reference is made to FIG. 4 as well.

In certain embodiments, the first extension channel 13 has the same depth as that of the first channel 1; the second extension channel 23 has the same depth as that of the second channel 2, such that it can simplify the fabrication process and ensure that cells and the drugs or cells that inhibit cell migration flow into corresponding extension channels effectively.

In certain embodiments, the first extension channel 13 and the second extension channel 23 have identical configuration, such that it can ensure a symmetrical migration and interference to the greatest extent and mitigate errors.

In certain embodiments, a plurality of the first channels 1 and the second channels 2 are provided on one microfluidic chip, and by this configuration, confined migration culturing of different cell types and co-culture screening assays of different drugs and cells on inhibiting the confined migration of target cells can be performed on the same microfluidic chip, so that unnecessary operations are avoided, and multiple results can be observed on one single chip.

In certain embodiments, two opposite ends of each of the second channels 2 are provided with the second inlet 11 and the second outlet 22, respectively, such that it can ensure that different drugs or cells are introduced through the channels for different processes and screenings.

Figure 2:
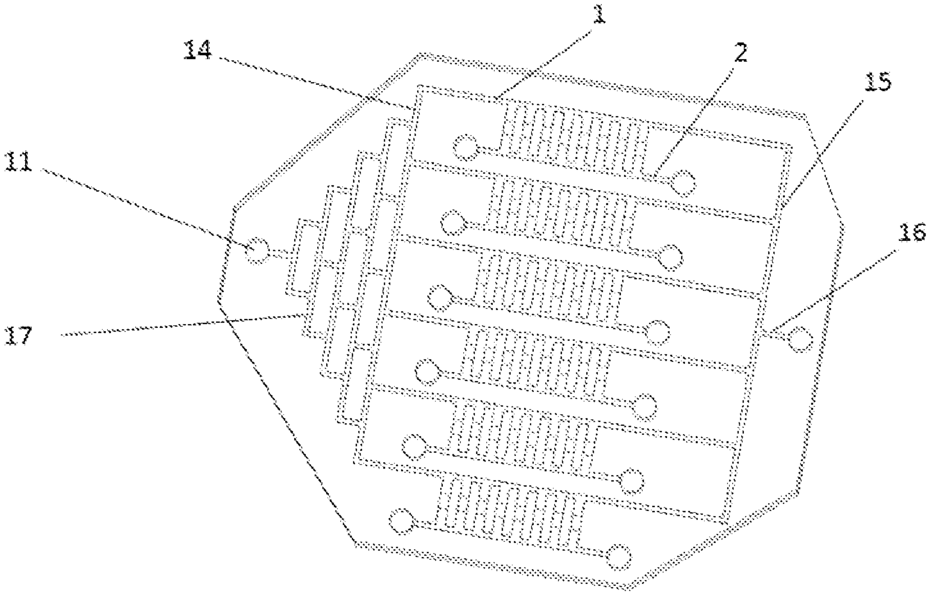
FIG. 2 schematically depicts an overall structure of an embodiment of the present invention, in which a plurality of the first channels and second channels are present and a pyramid-like flow diverging structure is used for diverging flows.

In certain embodiments, two opposite ends of each of the first channels 1 are provided with the first inlet 11 and the first outlet 12, respectively. In other embodiments, converging channels are further provided on the same chip at two opposite ends of the first channels 1 which channelize all the first channels 1. Turning to FIG. 2, each of the converging channels has an inlet converging channel 14 and an outlet converging channel 15, where the inlet converging channel 14 connects to the first inlet 11; and the outlet converging channel 15 connects to the first outlet 12. By this configuration, it can ensure that cells or drugs entering each of the first channels 1 are evenly distributed among different first channels.

In certain embodiments, the chip further includes an outlet connection channel 16 provided in a central part of the outlet converging channel 15; the outlet connection channel 16 connects the first outlet 12 and the outlet converging channel 15.

Figure 3:
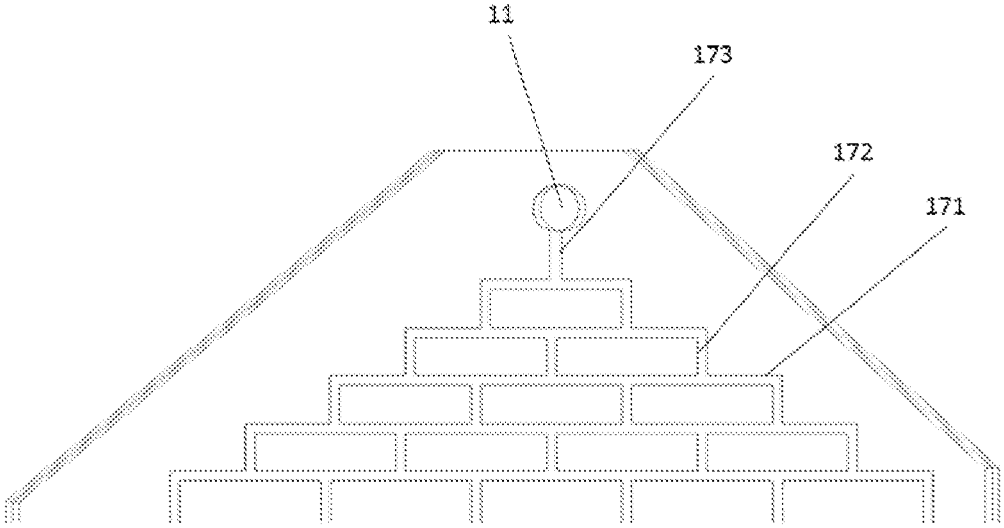
FIG. 3 shows a partially enlarged view of the structure of the pyramid-like flow diverging structure according to certain embodiments of the present invention.

In certain embodiments, to ensure that liquid flowing into each of the first channels 1 is completely the same with each other in terms of their content and volume, a pyramid-like flow diverging structure 17 is further provided on the chip, and the number of flow channels at the most bottom (last stage) of the pyramid-like flow diverging structure 17 is equal to the number of the first channels 1; a top end of the pyramid-like flow diverging structure 17 is connected to the first inlet 11. A good flow diverging effect among the first channels 1 is thereby achieved by providing the pyramid-like flow diverging structure 17, thereby avoiding occurrence of uneven flow distribution. In certain embodiments, the pyramid-like flow diverging structure 17 is a gradient flow diverging structure, and each subsequent layer (stage) is added with one flow channel with respect to the number of flow channels of its preceding layer, such that a more even flow distribution is achieved. The pyramid-like flow diverging structure 17 includes multiple layers (stages) of flow diverging channels, and each level (stage) of flow diverging channels includes a lateral channel 171 and a longitudinal diverging channel 172; the longitudinal diverging channel 172 of a preceding stage connects to the lateral channel 171 of its subsequent stage; the lateral channels 171 of the last stage connect to all the first channels 1; a top layer of the pyramid-like flow diverging structure 17 only includes one diverging channel 173, which is a first diverging channel in longitudinal flow direction, and the first diverging channel 173 connects the first inlet 11 and a second-stage lateral channel 171. Reference is also made to FIG. 3.

In certain embodiments, each of the longitudinal channel 172 and the lateral channel 171 has a depth identical to that of the first channel 1.

Turning to FIG. 4, in certain embodiments, the microfluidic chip includes an upper chip 41 and a lower chip 42, wherein the upper chip 41 is provided therethrough with the first inlet 11, the second inlets 21, the first outlet 12 and the second outlets 22; the upper chip 41 and the lower chip 42 are associated with each other to form the complete microfluidic chip; the first channel 1, the second channel 2, the first extension channel 13, the second extension channel 23 and the confined migration channels 3 are formed between the upper chip 41 and the lower chip 42. This configuration can allow the provision of channels between the two chips more easily, and thus effectively avoid the pollution caused by cell exposure.

In certain embodiments, the upper chip 41 includes an upper channel section; the lower chip 42 includes a lower channel section; and the upper channel section and the lower channel section are combined to form all the channels.

In certain embodiments, the upper chip 41 includes an upper set of the first channels 1, an upper set of the second channels 2 and an upper set of the confined migration channels 3; the lower chip 42 includes a lower set of the first channels 1, a lower set of the second channels 2 and a lower set of the confined migration channels 3; a sum of the depth of the upper first channels 1 and that of the lower first channels 1 is equal to the sum of the depth of the first channels 1; a sum of the depth of the upper second channels 2 and that of the lower second channels 2 is equal to the sum of the depth of the second channels 2; a sum of the depth of the upper confined migration channels 3 and that of the lower confined migration channels 3 is equal to the sum of the depth of the confined migration channels 3.

In certain embodiments, the channel portions of the upper chip 41 and those of the lower chip 42 are identical, and the confined migration channels 3 is centered between the first extension channel 13 and the second extension channel 23.

In another embodiment, a depth of all the channel portions of the upper chip 41 or the lower chip 42 is equal to that of the confined migration channel 3, and no channel is provided in a corresponding portion of the lower chip 42 or in a corresponding portion of the upper chip 41 with respect to the confined migration channel 3.

Figure 6:
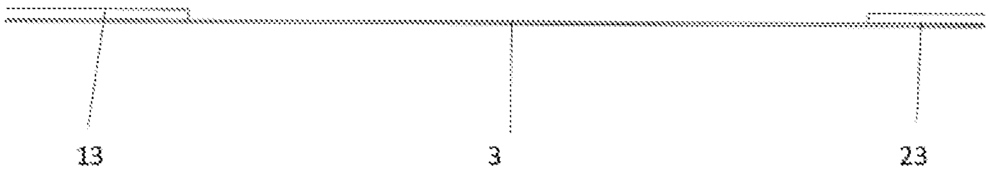
FIG. 6 shows a partially enlarged, cross-sectional view of the longitudinal structure of the first extension channel, the confined migration channel, and the second extension channel according to certain embodiments of the present invention.

In certain embodiments, the depth of all the channel portions of the lower chip 42 is equal to that of the confined migration channel 3, and no channel is provided in a corresponding portion of the upper chip 41 with respect to the confined migration channel 3, forming the confined migration channel 3. Exclusive of the corresponding portion with respect to the confined migration channel 3, a depth of the other channel portions of the upper chip 41 is equal to the difference between the total channel depth (i.e., the sum of the depth of other channel portions of the upper chip 41 and the depth of all the channel portions of the lower chip 42) and the depth of the confined migration channel 3. Reference is made to FIG. 6.

In certain embodiments, the depth of the confined migration channel 3 is in a range of 4-10 microns; the depth of the other channels excluding the confined migration channel 3 is in a range of 20-40 microns. By this configuration, it can effectively enable the cell culture and establishment of a confined migration environment.

In certain embodiments, the depth of the confined migration channel 3 is 6 microns; the depth of the other channels is 30 microns.

In certain embodiments, excluding the corresponding portion with respect to the confined migration channel 3 that has no depth, the depth of the other channel portions of the upper chip 41 is 24 microns; the depth of all the channels of the lower chip 42 is 6 microns.

In certain embodiments, a width of all the channels is in a range of 40-60 microns;

In certain embodiments, a length of the first extension channel 13 or a length of the second extension channel 23 is in a range of 60-80 microns;

In certain embodiments, a length of the confined migration channel 3 is in a range of 40-60 microns;

In certain embodiments, each of the confined migration channels 3 has a uniform square cross-section and identical dimension (length and width) with each other; the length and the width of each of the confined migration channels are 50 microns each.

In certain embodiments, the microfluidic chip or chips is/are made of polydimethylsiloxane (PDMS).

In certain embodiments, the microfluidic chip or chips is/are polygonal or circular.

In certain embodiments, the microfluidic chip or chips is/are octagonal, or in a shape according to the embodiments depicted in any of FIGS. 2, 4, 7 and 8.

In certain embodiments, a material that enhances cell adhesion is incorporated into the channels, wherein the material is selected from fibronectin.

In certain embodiments, the present device further includes an accommodation structure 5 capable of accommodating a plurality of chips, and the accommodation structure 5 is provided with a plurality of chip placement holes or slots 51 each for accommodating one chip. By this configuration, a plurality of chips can be placed on the accommodation structure 5 and analyzed simultaneously, such that image analyses of a plurality of chips can be performed in one time, and it is not necessary to repeatedly place and remove the chips. In case where some studies require analyzing multiple chips, a one-time analysis of multiple chips is feasible by the present invention, and the results are allowed to be directly presented on the same image.

Figure 7:
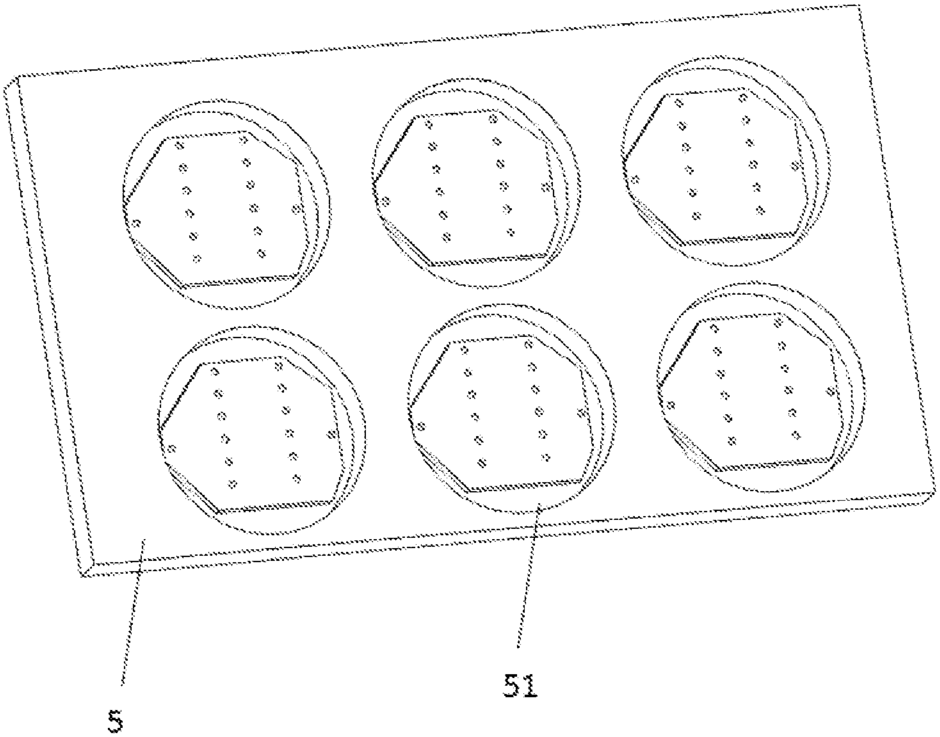
FIG. 7 schematically depicts the accommodation structure with a plurality of microfluidic chips according to certain embodiments of the present invention.
Figure 8:
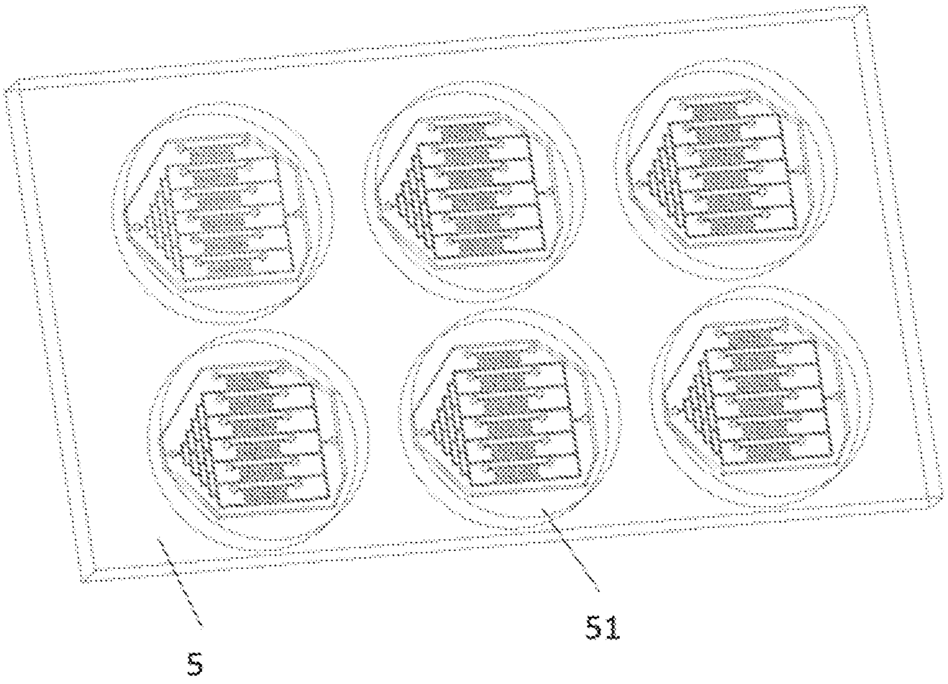
FIG. 8 shows a perspective view of the accommodation structure with a plurality of microfluidic chips according to certain embodiments of the present invention.

In certain embodiments, the chip placement holes or slots 51 are circular holes capable of accommodating the chip(s). This configuration as circular holes eases placing and removal of the chips from the device. Reference is made to FIGS. 7-8.

Example 2

Provided herein is a method for preparing the microfluidic chip or chips of the present invention, which includes:

1) constructing a chip mold (or template) for the upper and lower chip microstructures by using a soft lithography, wherein a material of the template is a silicon oxide wafer;
2) mixing polydimethylsiloxane (PDMS) and a curing agent in a ratio of 10:1 to prepare a modified PDMS, and removing microbubbles in the PDMS by degassing with a vacuum pump for 12-16 minutes;
3) pouring the modified PDMS onto the silicon wafer template, and then degassing for 12-16 minutes until the PDMS is completely attached to a surface of the wafer;
4) baking in an oven or drying in a desiccator at 65° C. for 100-150 minutes until the PDMS is completely cured and molded;
5) cutting out from the cured and molded PDMS a single structure and punching holes on the single structure at where the first inlet 11, second inlets 11, first outlet 12 and second outlets 22 are disposed on the chip by using a round punch having a diameter of 1.22 millimeters for punching each hole;
6) treating the single structure into an air plasma treatment system for 2 minutes, and then aligning the single structure under a microscope for bonding; and
7) sterilizing the single structure by using ultraviolet irradiation for 45 minutes, adding 2% fibronectin, and placing in an incubator at 37° C. for enhancement of cell adhesion inside the channels of the chip.

Example 3

Provided herein are different scenarios of applying the present invention according to various embodiments of providing a plurality of the first channels 1 and second channels 2 on a single chip and further providing the pyramid-like flow diverging structure 17:

(1) Method for Studying the Effect of Different Drugs or Different Concentrations of Various Drugs on Migration of a Single Type of Cells After the chip treatment is completed, a cell suspension is loaded into the first inlet 11 of the pyramid-like flow diverging structure 17. A pipette tip is used to slightly suction at the first outlet 12 to let the cells flow into the first channels 1 evenly, and then enter the first extension channels 13 evenly. Different drugs are loaded into the second inlets 11 of different second channels 2, respectively. The channels are photographed and observed for 48 hours in real time by using an Etaluma™ LS720 fluorescence microscope, and a cell migration image is taken every half an hour. The effect of different drugs or different concentrations of various drugs on the migration of the same type of cells is thereby evaluated.

(2) Method for Studying the Effect of a Drug on Migration of Different Cell Types After the chip treatment is completed, different cell suspensions are loaded into inlets of the second channels 2 of the chip, respectively, and allowed to wait for 1 minute until liquid in the channels is equalized and the cells completely flow into the second channels 2 and then enter the second extension channels 23. A drug-containing liquid is added into the first inlet 11 with respect to the pyramid-like flow diverging structure 17. A pipette tip is used to slightly suction to let the drug-containing liquid flow into the first channels 1 evenly and enter the first extension channels 13 evenly. The channels are photographed and observed for 48 hours in real time by using an Etaluma™ LS720 fluorescence microscope, and a cell migration image is taken every half an hour. The effect of a drug on the migration of different cells is thereby evaluated.

(3) Method for Studying the Effect of Cell-Cell Interaction in Co-Culture and Cell-Drug Interaction on Cell Migration After the chip treatment is completed, a co-culture cell medium, such as liquid containing tumor-associated fibroblasts, is added into the first inlet 11 of the pyramid-like flow diverging structure. A pipette tip is used to slightly suction to let the tumor fibroblasts-containing liquid flow into the first channels 1 evenly and enter the first extension channels 13 evenly; tumor cells and drug liquid are added into the second inlet 11 of the second channels 2, so that the tumor cells and the drug liquid enter the second extension channels 23. The channels are photographed and observed for 48 hours in real time by using an Etaluma™ LS720 fluorescence microscope, and a cell migration image is taken every half hour. The effect of the fibroblasts and the drug on the cell migration in real time is thereby evaluated.

Although the invention has been described in terms of certain embodiments, other embodiments apparent to those of ordinary skill in the art are also within the scope of this invention. Accordingly, the scope of the invention is intended to be defined only by the claims which follow.

What is claimed is:

1. A confined migration microfluidic device for cell culture and drug screening, comprising:

at least one microfluidic chip, each of the at least one microfluidic chip comprising:

a plurality of first channels;

a plurality of second channels each being disposed in parallel with one of the first channels thereby providing a plurality of pairs of the first channels and the second channels;

a plurality of confined migration channels;

a plurality of two extension channels;

each of the plurality of pairs of the first channels and the second channels being connected through the confined migration channels, each of the confined migration channels having a depth smaller than that of each of the first channels and second channels;

two opposite ends of each of the first channels being provided with a first inlet and a first outlet, respectively;

two opposite ends of each of the second channels being provided with a second inlet and a second outlet, respectively; and an upper chip and a lower chip, wherein the plurality of confined migration channels between each of the plurality of pairs of the first channel and the second channel being identical in terms of shape and dimension;

the plurality of two extension channels each composed of a first extension channel and a second extension channel being respectively disposed at two opposite ends of each of the confined migration channels;

the first extension channel communicating with the first channel and the confined migration channel;

the second extension channel communicating with the second channel and the confined migration channel;

each of the first extension channel and the second extension channel having a depth greater than that of the confined migration channel; and wherein the upper chip is provided therethrough with the first inlet, the second inlet, the first outlet, and the second outlet, and wherein the upper chip and the lower chip are associated with each other to form each of the at least one microfluidic chip, and wherein the first channels, the second channels, the first extension channels, the second extension channels, and the confined migration channels are formed between the upper chip and the lower chip, and wherein the upper chip comprises upper channel portions; the lower chip comprises lower channel portions, and wherein the upper channel portions and the lower channel portions are combined to form all channels, and wherein the upper chip further comprises an upper set of the first channels, an upper set of the second channels, and an upper set of the confined migration channels; the lower chip further comprises a lower set of the first channels, a lower set of the second channels, and a lower set of the confined migration channels, and wherein a sum of a depth of each of the upper first channels and that of each of the lower first channels is equal to a sum of a depth of each of the first channels; a sum of a depth of each of the upper second channels and that of each of the lower second channels is equal to a sum of a depth of each of the second channels; a sum of a depth of each of the confined migration channels of the upper set of the confined migration channels and that of each of the confined migration channels of the lower set of the confined migration channels is equal to a sum of a depth of each of the confined migration channels.

2. The microfluidic device according to claim 1, wherein the plurality of identical confined migration channels comprises four to ten identical confined migration channels provided between each of the plurality of pairs of the first channel and the second channel.

3. The microfluidic device according to claim 2, wherein the four to ten identical confined migration channels comprises four, six, eight, or ten identical confined migration channels between each of the plurality of pairs of the first channel and the second channel.

4. The microfluidic device according to claim 1, wherein each of the first extension channels has a depth identical to that of each of the first channels; each of the second extension channels has a depth identical to that of each of the second channels.

5. The microfluidic device according to claim 4, wherein the first extension channels and the second extension channels are identical to each other.

6. The microfluidic device according to claim 1, further comprising converging channels provided on each of the at least one microfluidic chip, and the converging channels being disposed at two opposite ends of each of the first channels and configured to channelize all of the first channels.

7. The microfluidic device according to claim 6, wherein each of the converging channels has an inlet converging channel and an outlet converging channel, and wherein the first inlet connects to the inlet converging channel and the first outlet connects to the outlet converging channel, and wherein each of the at least one microfluidic chip further comprises an outlet connection channel provided at a central part of the outlet converging channel; the outlet connection channel connects the first outlet and the outlet converging channel.

8. The microfluidic device according to claim 6, further comprising a pyramid-shaped flow diverging structure provided on each of the at least one microfluidic chip, wherein the number of flow channels at a last level of the pyramid-shaped flow diverging structure is equal to the number of the first channels, and wherein a top end of the pyramid-shaped flow diverging structure connects to the first inlet.

9. The microfluidic device according to claim 8, wherein the pyramid-shaped flow diverging structure is a gradient flow diverging structure, and wherein each subsequent gradient layer is added with one flow channel with respect to a preceding layer.

10. The microfluidic device according to claim 8, wherein the pyramid-shaped flow diverging structure comprises multiple levels of flow diverging channels, and each level of the flow diverging channels comprises a lateral channel and a longitudinal channel, wherein the longitudinal channel of a preceding level connects to the lateral channel of a subsequent level, wherein the lateral channel of the last level connects all the first channels, and wherein the pyramid-shaped flow diverging structure has a top layer comprising only a first longitudinal channel, and the first longitudinal channel connects the first inlet and the lateral channel of a second stage of the pyramid-shaped flow diverging structure, and wherein each of the longitudinal channels and the lateral channels has a depth equal to that of the first channel.

11. The microfluidic device according to claim 1, wherein the upper channel portions and the lower channel portions are identical, and each of the confined migration channels are centered between each of their corresponding first extension channel and their corresponding second extension channel.

12. The microfluidic device according to claim 1, wherein a depth of all the upper channel portions and the lower channel portions is equal to that of the confined migration channels.

13. The microfluidic device according to claim 12, wherein the depth of all channel portions of the lower chip is equal to that of the confined migration channels, and no channel is provided in the corresponding portion of the upper chip with respect to the confined migration channels.

14. The microfluidic device according to claim 1, wherein each of the confined migration channels has a depth in a range of 4-10 microns; each channel other than the confined migration channels has a depth in a range of 20-40 microns; a width of the all the channels is in a range of 40-60 microns; a length of the first extension channels or a length of the second extension channels are in a range of 60-80 microns; a length of the confined migration channels are in a range of 40-60 microns; each of the confined migration channels has identical length, width, and cross-section with each other.

15. The microfluidic device according to claim 1, further comprising a material that enhances cell adhesion and is incorporated into all channels, wherein the material is selected from fibronectin.

16. The microfluidic device according to claim 1, further comprising an accommodation structure capable of accommodating the at least one microfluidic chips, wherein the accommodation structure is provided with at least one microfluidic chip placement holes or slots each for accommodating one of the at least one microfluidic chips, and wherein the at least one microfluidic chip placement holes or slots are circular holes capable of accommodating the at least one microfluidic chip to enable placing and removal of the at least one microfluidic chip.

17. The microfluidic device according to claim 1, wherein cells of the cell culture are normal cells or disease cells; and wherein the normal cells comprise kidney cells, lung cells, digestive tract cells, brain cells, liver cells, fibroblasts, endothelial cells, immune cells, and macrophages; and wherein the disease cells are tumor cells derived from abnormal cells, tumor-associated macrophages, or tumor-associated fibroblasts; and wherein the tumor cells derived from abnormal cells comprise gastric cancer cells, pancreatic cancer cells, colorectal cancer cells, liver cancer cells, bone cancer cells, lung cancer cells, kidney cancer cells, prostate cancer cells, breast cancer cells, brain cancer cells, and neuroendocrine tumor cells.

* * * * *